(12) United States Patent
Will et al.

(10) Patent No.: US 9,615,944 B2
(45) Date of Patent: Apr. 11, 2017

(54) COUPLABLE PROSTHETIC DEVICE

(71) Applicant: Rocky Mountain Manufacturing, LLC, Grand Junction, CO (US)

(72) Inventors: Michael W. Will, Montrose, CO (US); Mark A. Lewis, Grand Junction, CO (US)

(73) Assignee: ROCKY MOUNTAIN MANUFACTURING, LLC., Grand Junction, CO (US)

( * ) Notice: Subject to any disclaimer, the term of this patent is extended or adjusted under 35 U.S.C. 154(b) by 0 days.

(21) Appl. No.: 14/461,097

(22) Filed: Aug. 15, 2014

(65) Prior Publication Data
US 2014/0358248 A1    Dec. 4, 2014

(51) Int. Cl.
*A61F 2/76* (2006.01)
*A61F 2/60* (2006.01)
*A61F 2/78* (2006.01)
*A61F 2/50* (2006.01)

(52) U.S. Cl.
CPC ............ *A61F 2/78* (2013.01); *A61F 2/60* (2013.01); *A61F 2/76* (2013.01); *A61F 2002/5072* (2013.01); *A61F 2002/5073* (2013.01); *A61F 2002/5083* (2013.01); *A61F 2002/5084* (2013.01); *A61F 2002/607* (2013.01); *A61F 2002/7868* (2013.01)

(58) Field of Classification Search
CPC ...... A61F 2/76; A61F 2/78; A61F 2002/5084; A61F 2/60; A61F 2/601
See application file for complete search history.

(56) References Cited

U.S. PATENT DOCUMENTS

| | | | |
|---|---|---|---|
| 1,319,884 A * | 10/1919 | McKay | ........................... 623/63 |
| 3,659,294 A | 5/1972 | Glabiszewski | |
| 4,007,496 A | 2/1977 | Glabiszewski | |
| 4,536,898 A | 8/1985 | Palfray | |
| 4,608,054 A | 8/1986 | Schroder | |
| 4,795,474 A | 1/1989 | Horvath | |
| 4,938,775 A | 7/1990 | Morgan | |
| 4,969,911 A | 11/1990 | Greene | |
| 5,047,063 A | 9/1991 | Chen | |
| 5,163,965 A | 11/1992 | Rasmusson et al. | |
| 5,376,129 A | 12/1994 | Faulkner et al. | |
| 5,425,782 A | 6/1995 | Phillips | |
| 5,443,526 A | 8/1995 | Hoerner | |
| 5,458,657 A | 10/1995 | Rasmusson | |
| 5,482,513 A | 1/1996 | Wilson | |

(Continued)

OTHER PUBLICATIONS

Racer Industries QuickCar Disconnect Button Style, www.racerindustries.com; Copyright 2012.

(Continued)

*Primary Examiner* — Marcia Watkins
(74) *Attorney, Agent, or Firm* — Jeffrey K. Riddle; Fabian VanCott

(57) ABSTRACT

A prosthetic device comprising an upper member, and a lower member having a conical terminating section, the conical terminating section fitting into a conical void defined in the upper member. A prosthetic device kit, comprising an upper member and a number of lower members each having a conical terminating section in which the conical terminating sections of each lower member fit into a conical void defined in the upper member.

19 Claims, 5 Drawing Sheets

(56) References Cited

U.S. PATENT DOCUMENTS

| | | |
|---|---|---|
| 5,507,837 A | 4/1996 | Laghi |
| 5,529,576 A | 6/1996 | Lundt et al. |
| 5,545,230 A | 8/1996 | Kinsinger et al. |
| 5,549,710 A | 8/1996 | Vera et al. |
| 5,759,206 A | 6/1998 | Bassett |
| 5,888,214 A * | 3/1999 | Ochoa ................. A61F 2/60 623/27 |
| 6,013,105 A | 1/2000 | Potts |
| 6,033,440 A | 3/2000 | Schall et al. |
| 6,231,618 B1 | 5/2001 | Schall et al. |
| 6,312,475 B1 | 11/2001 | Voisin |
| 6,797,008 B1 | 9/2004 | Arbogast et al. |
| 6,972,042 B2 | 12/2005 | Benson |
| 7,235,108 B2 | 6/2007 | Carstens |
| 7,288,116 B2 | 10/2007 | Ikeda |
| 7,288,117 B2 | 10/2007 | Benson |
| 7,563,288 B2 | 7/2009 | Doddroe et al. |
| 8,641,780 B2 | 2/2014 | Abimosleh et al. |
| 2004/0068325 A1 | 4/2004 | Phillips et al. |
| 2005/0049720 A1* | 3/2005 | Benson ................. 623/38 |
| 2005/0203638 A1 | 9/2005 | Slemker et al. |
| 2007/0255425 A1 | 11/2007 | Weihermuller |
| 2009/0292368 A1 | 11/2009 | Plowman et al. |
| 2011/0015761 A1 | 1/2011 | Celebi et al. |

OTHER PUBLICATIONS

Ferrier Couler Inc., vol. 7, Innovative Options for Prosthetics Brochure, www.ferrier.coupler.com; copyright 2013.

\* cited by examiner

COUPLABLE PROSTHETIC DEVICE

BACKGROUND

The present application generally relates to a prosthetic device. Prosthetic devices provide additional mobility to those persons with limited mobility due to a missing limb. These devices allow a recipient to accomplish those physical tasks of others not missing the limb.

BRIEF DESCRIPTION OF THE DRAWINGS

The accompanying drawings illustrate various examples of the principles described herein and are a part of the specification. The examples do not limit the scope of the claims.

Throughout the drawings, identical reference numbers designate similar, but not necessarily identical, elements.

DETAILED DESCRIPTION

Figure 1:
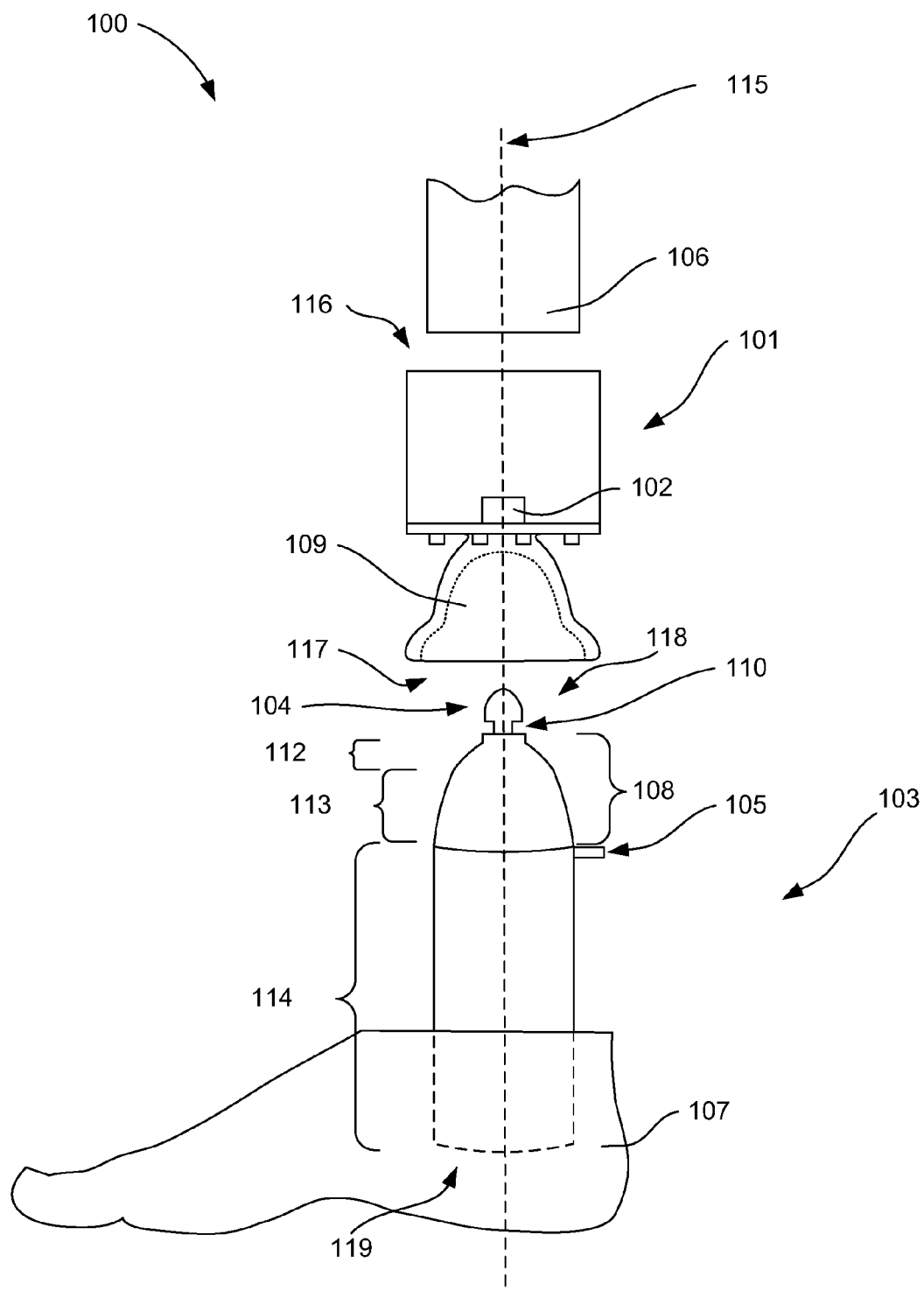
FIG. 1 is a side exploded elevation view of a prosthetic device according to one example of principles described herein.

As briefly described above, prosthetic devices allow additional mobility for a recipient that would not otherwise be available to the amputee. Some prosthetic devices are awkward, expensive and not user friendly. Specifically, prosthetic foot and leg attachments are rigid and difficult to remove with one hand. Where the prosthetic device is a prosthetic leg, the prosthetic leg may make it difficult for the user to put on and take off pants because the user is left to take the entire prosthetic device off before putting on or taking of pants. Alternatively, the user may attempt to slide the pants over the attached prosthetic device. This may prove difficult as the shoe and leg portions of the prosthetic device form a 90° angle, making such a task difficult if not impossible. Further, some devices do not accommodate different types of users' feet and shoes and consequently it may not be easy to adjust these devices for the individual types of shoes.

Also, existing prosthetic foot devices do not allow the user to easily adjust the heel height of their prosthetic devices when changing into different shoes, because this too may involve tools to adjust the expensive and complex components of the leg pylon. This can be inconvenient for the amputee to reach in order to make the adjustment. Even further, if the user were to adjust the prosthetic in this manner, he or she may be adjusting the device incorrectly and/or contrary to how a trained doctor and/or prosthetists would adjust the device. Improper adjustment of the prosthetic device by a user may result in further debilitating illnesses associated with the user's muscle and bone structure.

The prosthetic device described herein is a device which, when attached to an amputee's prosthetic limb will provide a convenient and elegant solution to the difficulties that many amputees face during their daily routine. The device features two sections, an upper member and a lower member in which the upper member is selectively coupled to the bottom of a prosthetic limb, and the lower member is selectively coupled to the upper member. The lower member may have a prosthetic foot coupled to it such that the foot may be inserted into a shoe. The lower member may be quickly released from the upper member and may allow for any number of different lower members to be attached thereto and thereby allow a user to attach a number of different types of shoes to the user's prosthetic device. The prosthetic device may further comprise a conical mounting surface between the upper and lower members that distributes the load placed on the two members so that the device may support the weight of the user as well as additional weight that the user may carry. This may provide the amputee with many conveniences in his daily life.

The present application, therefore, describes a prosthetic device comprising an upper member and a lower member having a conical terminating section, the conical terminating section fitting into a conical void defined in the upper member.

The present application further describes a prosthetic device kit, comprising an upper member and a number of lower members each having a conical terminating section in which the conical terminating sections of each lower member fit into a conical void defined in the upper member.

The present application further describes an interlocking prosthetic device comprising an upper member selectively coupled at a proximal end to a terminating end of a prosthetic device and a lower member selectively coupled to a distal end of the upper member in which the distal end of the upper member comprises a conical void defined therein to receive a conical proximal end of the lower member.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language indicates that a particular feature, structure, or characteristic described in connection with that example is included as described, but may not be included in other examples.

In the present specification and in the appended claims, the term "prosthetic device" is meant to be understood broadly as any mechanical device by which an amputee uses as a replacement for a missing body part. Therefore, although the present application describes a prosthetic device that replaces a user's leg or single piece prosthetic device, the present application contemplates the use of the below described upper and lower members for any other missing body part including, for example, an upper arm, a lower arm, or a finger, among others Additionally, as used in the present specification and in the appended claims, the term "a number of" or similar language is meant to be understood broadly as any positive number comprising 1 to infinity; zero not being a number, but the absence of a number.

Turning now to the figures, FIG. 1 shows a side exploded elevation view of the prosthetic device (100) according to one example of the principles described herein. The prosthetic device may comprise an upper member (101) and a lower member (103). The upper member (101) may be selectively coupled to a distal end of a prosthetic limb (106) at a proximal end (116) of the upper member (101) and to the lower member (103) at a distal end (117) of the upper member (101). The lower member (103) may be selectively coupled to the upper member (101) at a proximal end (118) of the lower member (103) and a prosthetic foot or shoe (107) on a distal end (119) of the lower member (103).

The upper member (101) comprises a conical receiving void (109) that is designed to house and accept a conical terminating section (108) at the proximal end (118) of the lower member (103). Both the conical receiving void (109) and conical terminating section (108) may be comprised of high strength materials so that they are capable of supporting a significant load, including the weight of the user, additional weight carried by the user, and the components of the prosthetic device (100). In one example, the conical receiving void (109) of the upper member (101) has an interior bell shape. In one example, the conical receiving void (109) is constructed of high strength metal and is between 3 and 7 mm thick with the bottom of the conical receiving void (109) being the thickest part.

The upper member (101) may further comprise a release button (102) that may be operated using a single hand. This may allow the user to selectively release the lower member (103) from the upper member (101) when, for example, the user is getting dressed or undressed or when the user is switching to a different type of shoe attached to a separate lower member (103). The upper member (101) may further comprise a prosthetic device coupler (FIG. 5, 501) generally in the shape of a cylinder. The prosthetic device coupler (FIG. 5, 501) will be described in more detail below.

Although FIG. 1 shows positioning characteristics of the prosthetic limb (106), prosthetic device (100), and prosthetic foot/shoe (107) relative to each other, in one example the prosthetic device may be rotated about a common axis (115) of the prosthetic limb (106), prosthetic device (100), and prosthetic foot/shoe (107). Thus, the present specification contemplates a prosthetic device (100) where features thereof may be positioned around the common axis (115) but still serve similar functions as described herein.

As described above, the lower member (103) comprises a generally cylindrical shape with a conical terminating section (108) at the proximal end (118). The lower member (103) may be made of a high strength material designed to support a relatively substantial amount of weight; in some examples exceeding that of the user's body weight. In one example, the walls of a cylindrical section (114) of the lower member (103) are between 1 mm and 3 mm thick through the entire section, with the cylinder having a total diameter of 3 cm. Other examples of the cylindrical section (114) may comprise examples of larger or smaller wall thickness or larger or smaller diameters to fit the type, weight, and activity of the user implementing the prosthetic device (100). Other examples comprise varying the thicknesses or diameters of the cylindrical section (114) of the lower member (103) and all parts of the prosthetic device (100) in order to increase or decrease the load bearing capacity of the lower member (103) while increasing or decreasing the total weight of the prosthetic device (100).

The cylindrical section (114) can have any height that may be appropriate by the patient's prosthetists, with one example measuring between 3 and 4 cm high. At the top of the cylindrical section (114) is the protrusion (105), which is used to orient the lower member (103) correctly when mating with the upper member (101). The protrusion (105) may comprise a small cylindrical piece of material extending radially from the surface of the lower member (103). In one example the protrusion (105) is a rod approximately 3 to 5 mm long with a diameter of approximately 3 mm.

The conical terminating section (108) of the lower member (103) may have 2 degrees of taper, with a first part of the conical section (112) being steeper than a second part of the conical section (113). In one example, the walls of the conical terminating section (108) may be between 3 and 6 mm thick so as to provide sufficient load bearing strength for the prosthetic device (100). The conical shape of the conical terminating section (108) also aids in simplifying the mating process of the lower member (103) to the upper member (101). Coupled to the top the conical section (108) there is a locking head (104).

The locking head (104) may engage with a locking clip (FIG. 3, 302) located on the upper member (101). The locking head (104) and locking clip (FIG. 3, 302) together secure the lower member (103) to the upper member (101) when the conical terminating section (108) of the lower member (103) is inserted into the conical receiving void of the upper member (101). In one example, the locking head (104) is a hemispherical body mounted atop a small cylindrical pylon extending from the apex of the conical section (113) of the upper member (101). As such, the locking clip (FIG. 3, 302) may engage with a space (110) defined between the hemispherical body and the apex of the conical section (113).

In one example, the pylon has a diameter of between approximately 6 mm and 8 mm and a height of between approximately 5 mm and 7 mm. In this example, the hemispherical body atop the pylon has a larger diameter of between approximately 12 mm and 14 mm, and vertical radius of between approximately 8 mm and 10 mm. The locking head (104) allows the locking clip (FIG. 3, 302) of the upper member (101) to secure itself around the small cylindrical pylon of the locking head (104), being secured by the conical section below, and the elongated hemisphere above. The circular profile of the locking head (104) also simplifies the mating process by allowing the locking head (104) to enter into the locking void of the upper member (101) from any angle.

Figure 2:
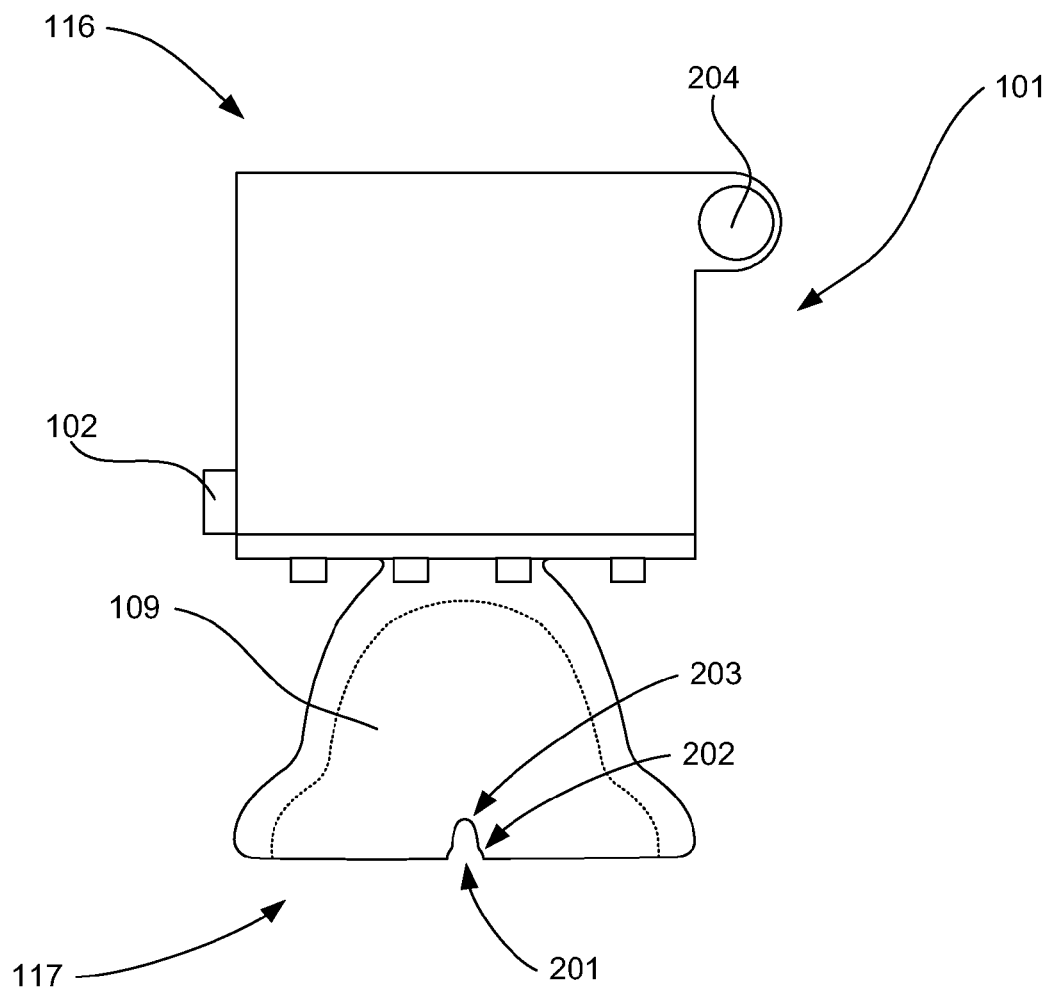
FIG. 2 is a side elevation view of the upper member of the prosthetic device according to one example of principles described herein.

FIG. 2 shows a rotated elevation view of the upper member (101). Shown in FIG. 2 is a guiding feature (201) which works in conjunction with the protrusion (105) on the lower member (103) to guide the locking head (104) into the locking clip (FIG. 3, 302) and properly align the upper member (101) with the lower member (103). The guiding feature (201) is composed of a guiding track (202) and a guiding notch (203). The guiding track (202) is a slightly angled taper which will guide the protrusion (105) of the lower member (103) around the edge of the conical receiver void (109) until the protrusion (105) securely houses itself in the guiding notch (203) found in the guiding feature (201). In one example the guiding track (202) may run 10 to 20 mm along the circumference of the conical receiver void (109). In other examples the guiding track (202) may run along the entire circumference of the conical receiver void (109) such that, as the lower member (103) is engaged with the upper member (101), the slope of the circumference of the conical receiver void (109) created by the guiding track (202) will guide the protrusion (105) into the guiding notch (203) wherever the protrusion (105) comes in contact with the circumference of the conical receiver void (109). The guiding notch (203) is a truncated cylindrical cutout from circumference of the conical receiver void (109) which is sufficiently sized to fit and secure the protrusion (105) therein. In one example, the guiding notch (203) has a partial circular vertical cross-section such that at least half of the interior surface of the guiding notch (203) comes in contact with the outer surface of the protrusion (105).

The upper member (101) may further comprise a tightening screw (204) to secure the distal end of a prosthetic limb (106) with the upper member (101). In one example, the tightening screw (204) may comprise a screw traversing through a separated portion of the upper member (101) such that tightening of the screw closes the separated portion of the upper member (101) thereby reducing the overall diameter of the upper member (101). In one example, the tightening screw (204) may be a quick release device that allows easy attachment of the upper member (101) to the prosthetic limb (106). In another example, the tightening screw (204) may comprise a screw that is not easily adjusted by a user of the prosthetic device (FIG. 100). In this example, the screw may comprise an engagement head such that a tool not readily accessible to a common consumer is implemented in order to manipulate the screw. In this example, this may be done so as to prevent the user of the prosthetic device (FIG. 1, 100) from adjusting the upper member (101)/prosthetic limb (106) interface thereby preventing improper adjustment of the prosthetic device (100) by the user. In another example, the upper member (101) may be adhesively bonded to the prosthetic limb (106). In this example, the tightening screw (204) is not used to secure the upper member (101) to the prosthetic limb (106) thereby eliminating weight and additional components.

Figure 3:
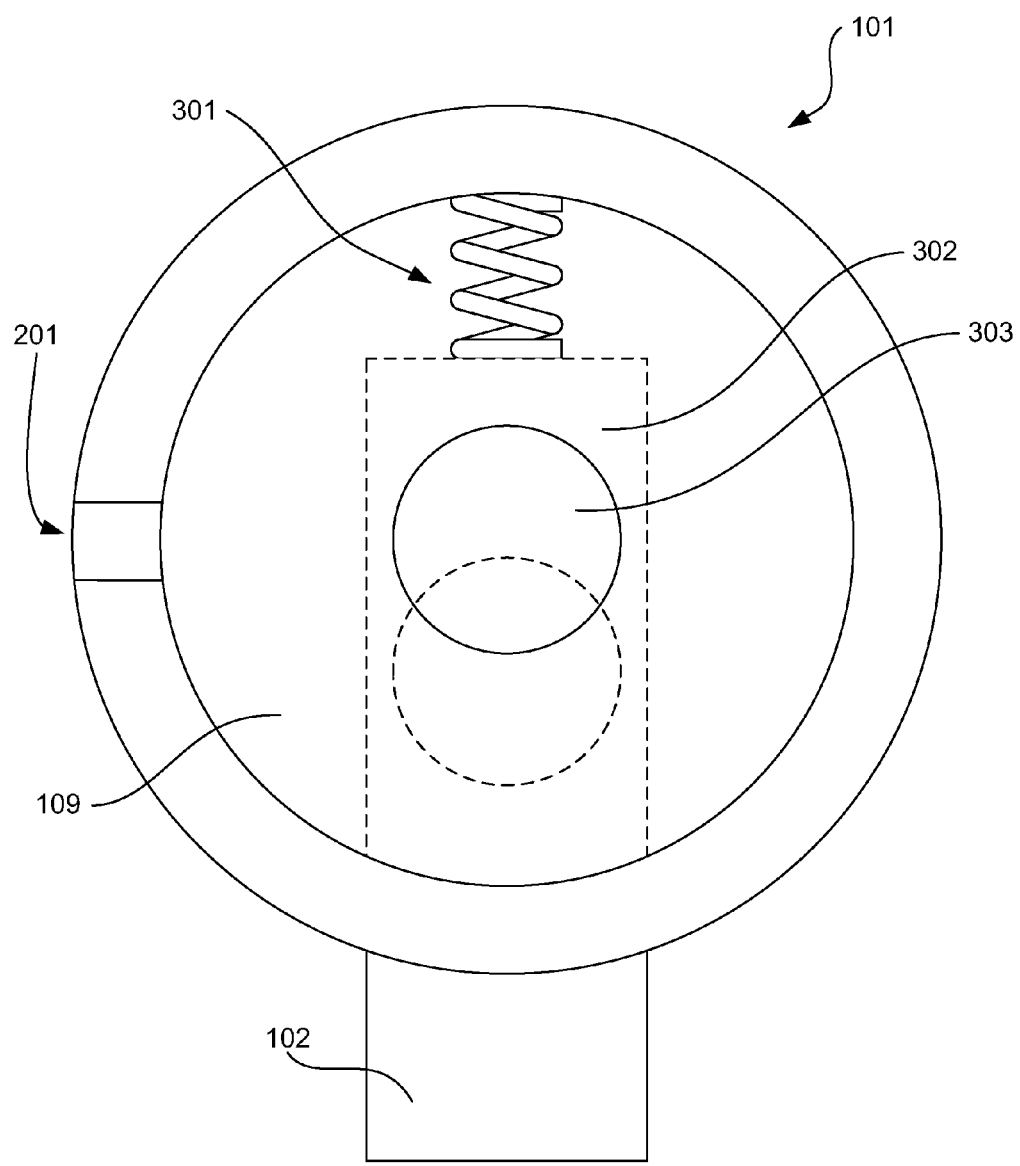
FIG. 3 is a top cross sectional view illustrating a prosthetic device locking feature according to one example of principles described herein.

FIG. 3 shows a bottom view cutout of the locking features of the upper member (101). FIG. 3 shows the functions of the locking mechanism that secure the locking head (104) of the upper member (101). The locking head (104) is shaped and sized so that it can pass through a circular opening of a circular receiver void (303). Upon entering the cavity, the hemispherical top of the locking head (104) will exert force on an upper locking clip (302) such that the force depresses a spring (301) biased radially inward relative to a common axis (115) of the upper (101) the lower members (103). Once the hemisphere of the locking head (104) has pushed past the upper locking clip (302), the spring (301) may extend the locking clip (302) back into its original position to secure and edge of the upper locking clip (302) against the pylon of the locking head (104), preventing the separation of the lower member (103) from the upper member (101) and securely mating the two together. To remove the upper member (101) from the lower member (103), the release button (102) may be depressed. The depression of the release button (102) pushes the upper locking clip (302) back away from the pylon and compresses the spring (301). This releases the tension on the lower member's (103) locking head (104) and allows for the easy separation of the two members (FIG. 1, 101 and 103). The release button (102) uses minimal force to depress, such that it may be operated with one hand or even one finger, freeing the other hand to perform other tasks.

Figure 4:
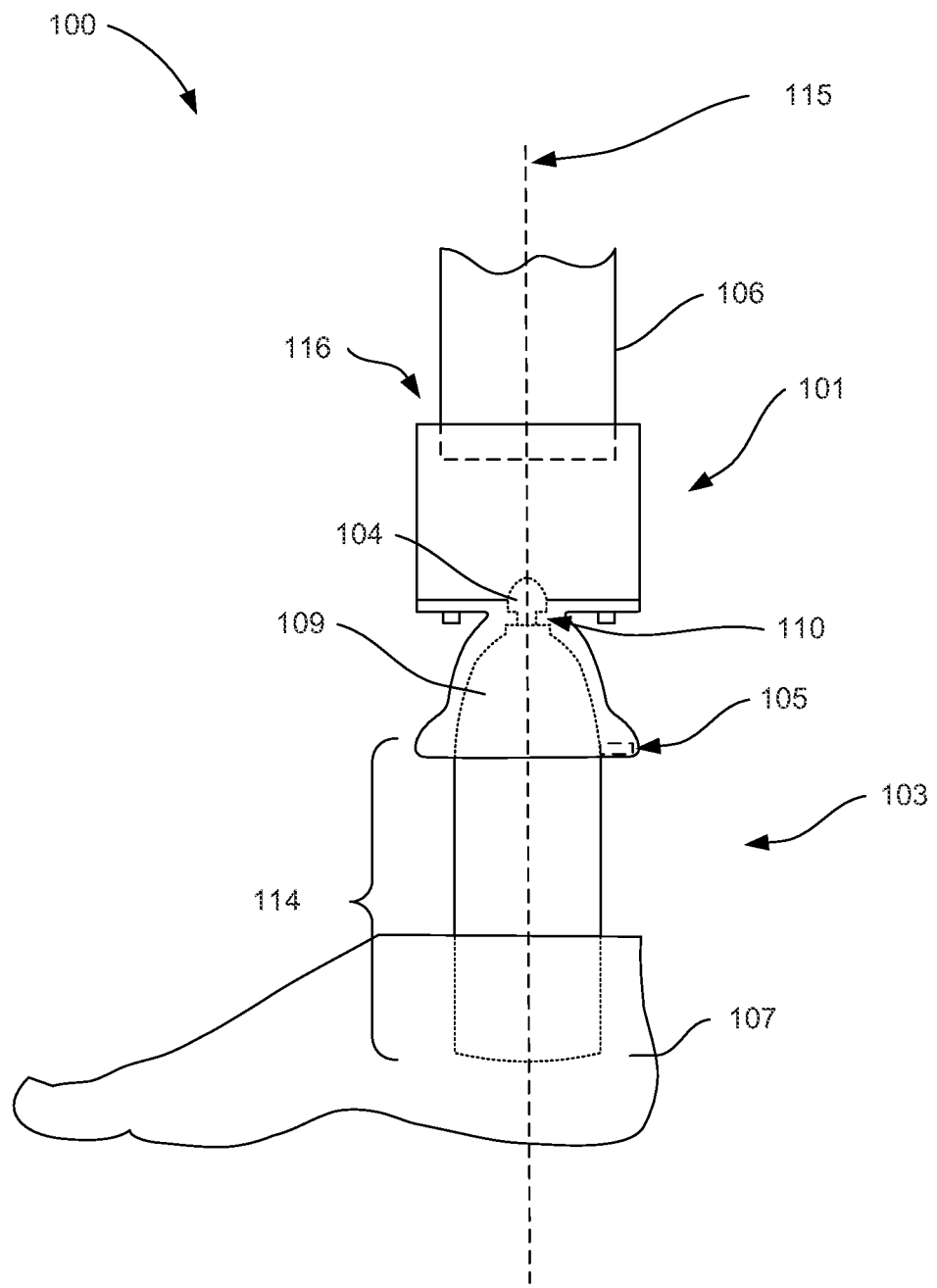
FIG. 4 is a side elevation cross sectional view illustrating the internal workings of the prosthetic device according to one example of principles described herein.

FIG. 4 is a front elevation cutout view of the prosthetic device (100) which further demonstrates the mating position of the upper member (101) and lower member (103). FIG. 4 shows one example of the contact points between the conical terminating member (108) of the lower member (103) and the conical receiving void (109) of the upper member (101). The cone shape of the two members effectively distributes the weight across the entire area of the interface. This figure also shows how the locking head (104) is secured by the locking clip (302).

Figure 5:
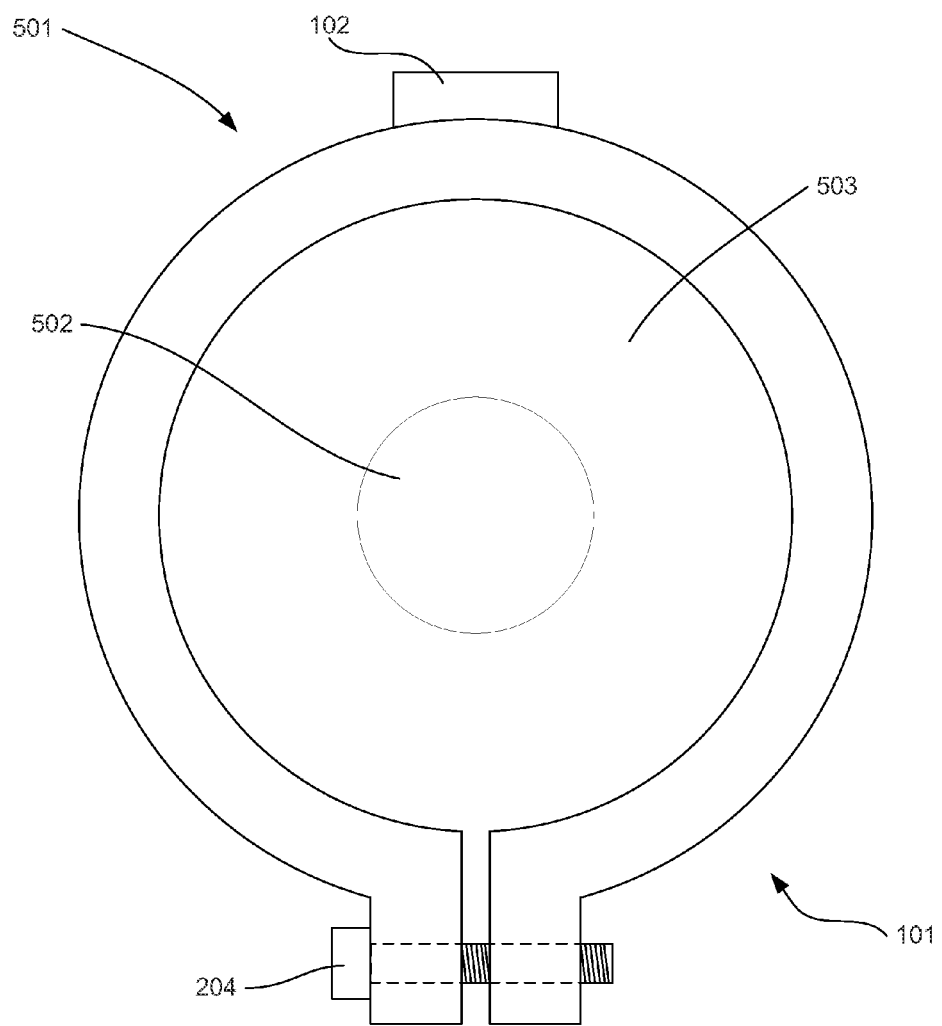
FIG. 5 is a top view of the upper member (101) shown in FIG. 1 according to one example of the principles described herein.

FIG. 5 is a top view of the upper member (101) shown in FIG. 1. FIG. 5 shows a void into which a user may mount a prosthetic limb (FIG. 1, 106) into in order to selectively attach the prosthetic limb (FIG. 1, 106) to the upper member (101). A prosthetic limb mounting area (503) may comprise a cylindrical impression between 2 and 3 cm deep, with a diameter of approximately 3 cm in one example. However, the mounting area (503) may be any size in order to properly mount any prosthetic limb to the upper member (101). The upper member (101) may comprise a small cylindrical housing (502) which houses the locking head (104) of the lower member (103) when the lower member (103) and upper member (101) are coupled together. The housing (502) may extend between 0.5 cm and 1 cm above the mounting area (503) and may have a diameter of between 1 cm and 1.5 cm.

The prosthetic limb (106), being a hollow cylindrical body, may encompass the housing (502) and then, in one example, be able to be tightened onto the upper member (101) using a tightening screw (FIG. 2, 204) or a quick release mechanism. The prosthetic limb mounting area (503) may be slightly larger in diameter than the diameter of the cylindrical body of the prosthetic limb (FIG. 1, 106) such that the tightening screw (FIG. 2, 204), when fastened, will compress against the prosthetic limb (FIG. 1, 106) closing a tightening allowance between the prosthetic limb and the prosthetic limb mounting area (503). The tightening allowance may be a small gap approximately 1 mm wide. This allows the mounting area (503) to securely fasten to the prosthetic limb (FIG. 1, 106). As described above, in another example, the upper member (101) may be adhesively bonded to the prosthetic limb (106), however, the prosthetic limb mounting area (503) may still be formed so as to receive the prosthetic limb (FIG. 1, 106).

The prosthetic device (FIG. 1, 100) described above may further be arranged in the form of a kit. In one example, the kit may comprise a single upper member (101) with a number of lower members (103). The upper member (101) may be coupled permanently or semi-permanently to a portion of the user's prosthetic device (FIG. 1, 100). Often a prosthetic device (FIG. 1, 100) comprises a cuff portion that wraps around a remaining portion of an amputee's limb. The cuff may be coupled to a rigid single tube that further couples to a prosthetic foot or shoe. The upper member described above may be attached to a terminal end of the tube. The attachment of the upper member (101) to the tube may be done by a trained technician and as such may be set permanently or semi-permanently to the tube of the existing prosthetic.

During this adjustment, the technician may further match the number of lower members (FIG. 1, 103) to the upper member (FIG. 1, 101). As described above, each lower member (FIG. 1, 103) comprises a protrusion (FIG. 1, 105) that mates with a guiding notch (FIG. 2, 203) on the upper member. As such, the technician may adjust any prosthetic foot or shoe (FIG. 1, 107) that is to be attached to the lower member (FIG. 1, 103) such that when the user couples the lower member (FIG. 1, 103) with the foot or shoe attached) to the upper member (FIG. 1, 101) the alignment is made to best accommodate the feel of the user. In this example, every lower member (FIG. 1, 103) the user couples to the upper member (FIG. 1, 101) will be properly aligned due to the protrusion (FIG. 1, 105) and the adjustments made by the technician with regards to the upper member/tube and lower member/shoe interfaces.

The specification and figures describe a prosthetic device that provides a user with the ability to detach the device from a prosthetic limb and self-align the device to the limb when re-attaching. This allows a user of the device to operate the release button (FIG. 1, 102) to detach the upper member (FIG. 1, 101) from the lower member (FIG. 1, 103) with one hand. Additionally, the conical shape of the interface between the two members (FIG. 1, 101, 103) provides for better weight distribution thereby allowing for less wear and tear on the device and greater comfort for the user. Still further, the spherical locking head (FIG. 1, 104) provide for easier insertion of a lower member (103) into the upper member (FIG. 1, 101) such that a user does not have to be as precise when engaging the two members. Still further, the device allows a user to selectively detach and reattach a number of lower members. These lower members (FIG. 1, 103) may be further coupled to a number of different foot wear such that a user may decouple the lower member (FIG. 1, 103) from the upper (FIG. 1, 101) when exchanging one type of shoe (i.e. dress shoe) for another type of shoe (i.e. running shoe). Additionally, by allowing the user to selectively remove the lower member (FIG. 1, 103) from the upper member (FIG. 1, 101) the user may more comfortably remove any pants or other clothing without having to remove their prosthetic device as well.

The preceding description has been presented to illustrate and describe examples of the principles described. This description is not intended to be exhaustive or to limit these principles to any precise form disclosed. Many modifications and variations are possible in light of the above disclosure.

What is claimed is:

1. A prosthetic device comprising:
   an upper member comprising;
      a guiding feature, comprising a sloped guiding track defined along a lip of a distal end of the upper member; and
   a lower member comprising:
      a conical terminating section formed at a proximal end of the lower member, the conical terminating section fitting into a conical void defined in the upper member and comprising a first conical part having a steeper angle than a second conical part relative to a common axis of the upper and lower members; a point of transition being formed between the first and second conical parts;
      a locking head coupled to a proximal end of the first conical part and fitting into a locking head void defined in the upper member; and
   a self-aligning feature comprising a protrusion extending radially from a section of the lower member and extending perpendicular to the common axis of the upper and lower members, in which the protrusion prevents the lower member from mating at an incorrect rotational position to the upper member;
      wherein contact of the self-aligning feature to the sloped guiding track as the conical terminating section is fitted into the conical void causes the lower member to rotate until the self-aligning feature is seated within a notch defined in the guiding feature.

2. The prosthetic device of claim 1, in which the upper member selectively attaches to a terminating member of a prosthetic limb.

3. The prosthetic device of claim 1, in which the sloped guiding track runs circumferentially along a portion of the lip of the distal end of the upper member.

4. The prosthetic device of claim 3, wherein the guiding track runs 20 mm along the lip of the distal end of the upper member.

5. The prosthetic device of claim 4, wherein the notch is cut out in a midway point along the sloped guiding feature.

6. The prosthetic device of claim 1, in which the upper member further comprises a locking mechanism to securely lock the upper member to the lower member.

7. The prosthetic device of claim 6, in which the locking mechanism comprises a spring loaded clip that locks the lower member to the upper member when the lower member is inserted into the upper member.

8. An interlocking prosthetic device comprising:
   an upper member selectively coupled at a proximal end of the upper member to a terminating end of a prosthetic limb; and
   a lower member selectively coupled to a distal end of the upper member and coupled, at a distal end of the lower member, with a prosthetic foot device;
   in which the distal end of the upper member comprises a conical void defined therein to receive a conical proximal end of the lower member;
   in which the conical proximal end of the lower member comprises:
      a first conical part having a steeper angle than a second conical part relative to a common axis of the upper and lower members; and a point of transition being formed between the first and second conical parts; and the lower member further comprising:
      a locking head coupled to the proximal end of the first conical part;
   in which the distal end of the upper member receiving the conical proximal end and locking head of the lower member is a monolithic piece; and
   in which the interlocking prosthetic device further comprises:
      a self-aligning feature comprising a protrusion protruding from the lower member perpendicularly to the common axis defined by the upper and lower members; and
      a guiding feature comprising a sloped guiding track defined in the distal end of the upper member and a guiding notch defined in the guiding feature, wherein the protrusion temporarily engages with the guiding track until the protrusion is seated within the guiding notch;
      wherein engagement of the protrusion with the guiding track via coupling of the upper member with the lower member causes the lower member to rotate about the common axis until the protrusion is seated within the guiding notch; and
      wherein the rotation of the lower member about the common axis aligns the prosthetic foot device with the prosthetic limb.

9. The prosthetic device of claim 7, wherein the spring loaded clip extends through the upper member forming a button actuatable by a user of the prosthetic device; actuation of the button causing the spring loaded clip to unlock the lower member from the upper member.

10. The prosthetic device of claim 7, wherein the spring loaded clip locks the lower member to the upper member by sliding in between a space defined between the locking head and the proximal end of the first conical part.

11. The interlocking prosthetic device of claim 8, in which a portion of the guiding track is sloped to direct the self-aligning feature into the guiding notch and wherein the guiding track directs the self-aligning feature into the guiding notch wherever the self-aligning feature comes in contact with the guiding track.

12. A prosthetic device kit, comprising:
    an upper member; and a number of lower members each having a conical terminating section at a proximal end thereof; each conical terminating section comprising a first conical part having a steeper angle than a second conical part relative to a common axis of the upper and lower members;

in which the conical terminating section of each lower member fits into a conical void defined in the upper member; the conical void providing a fit with each of the first and second conical parts;

in which a locking head is coupled to the proximal end of each of the lower members, each of the locking heads selectively fitting into a locking head void defined in the upper member; and in which each of the lower members comprises a self-aligning feature comprising a protrusion extending perpendicularly and radially from the common axis of the upper and lower members.

13. The prosthetic device kit of claim 12, in which the upper member is selectively attachable to each one of the number of lower members.

14. The prosthetic device kit of claim 12, in which each of the lower members is selectively coupled to a prosthetic foot.

15. The prosthetic device kit of claim 12, in which the upper member further comprises a guiding track that steers the self-aligning feature extending from any of the lower members into a guiding notch defined in the guiding track.

16. The prosthetic device kit of claim 15, in which a portion of the guiding track is sloped to cause the self-aligning feature to be steered into the guiding notch and wherein the guiding track directs the self-aligning feature into the guiding notch wherever the self-aligning feature comes in contact with the guiding track.

17. The prosthetic device kit of claim 16, in which a distal end of each of the conical terminating sections is coupled to a prosthetic foot and in which setting of the protrusion into the guiding notch aligns the prosthetic foot with the upper member secured to a prosthesis of a user.

18. The prosthetic device kit of claim 12, in which the upper member further comprises a securing device that secures the lower member to the upper member when the lower member is coupled to the upper member.

19. The prosthetic device kit of claim 18, in which the securing device comprises a locking clip that locks into place via a spring biased radially inward from the common axis of the upper and lower members.

\* \* \* \* \*